United States Patent
Hoshiko et al.

[11] Patent Number: 6,114,292
[45] Date of Patent: Sep. 5, 2000

[54] HEMATOLOGICAL ANALYZER SAMPLING PROBE CLEANSING METHOD

[75] Inventors: Susumu Hoshiko, Kobe; Miki Miyaji, Akashi, both of Japan

[73] Assignee: Sysmex Corporation, Kobe, Japan

[21] Appl. No.: 09/487,629

[22] Filed: Jan. 20, 2000

Related U.S. Application Data

[62] Division of application No. 09/161,672, Sep. 29, 1998, Pat. No. 6,043,205.

[30] Foreign Application Priority Data

Oct. 1, 1997 [JP] Japan ..................................... 9-268301

[51] Int. Cl.[7] ................................ C11D 1/72; C11D 3/30; C11D 7/08
[52] U.S. Cl. .......................... 510/161; 510/181; 510/405; 510/413; 510/421; 510/499; 134/22.1; 134/22.11; 134/22.12; 422/44; 422/50; 422/68.1
[58] Field of Search ................................ 134/22.1, 22.11, 134/22.12; 422/44, 50, 68.1; 510/161, 181, 405, 413, 421, 499

[56] References Cited

U.S. PATENT DOCUMENTS

| | | | |
|---|---|---|---|
| 4,855,130 | 8/1989 | Konrad et al. ............................. | 424/70 |
| 4,956,281 | 9/1990 | Wallner et al. ......................... | 435/69.3 |
| 4,957,842 | 9/1990 | Takahashi ................................ | 435/226 |
| 5,081,228 | 1/1992 | Dower et al. ........................... | 530/35.1 |
| 5,110,730 | 5/1992 | Edgington et al. ..................... | 435/69.6 |
| 5,395,545 | 3/1995 | Fischer et al. .......................... | 252/89.1 |
| 5,470,561 | 11/1995 | Klugkist et al. .......................... | 424/49 |
| 5,749,976 | 5/1998 | Fischer et al. ........................ | 134/22.12 |
| 5,888,752 | 3/1999 | Malin et al. ............................ | 435/7.24 |

*Primary Examiner*—Yogendra Gupta
*Assistant Examiner*—Charles Boyer
*Attorney, Agent, or Firm*—Shinjyu An Intellectual Property Firm

[57] ABSTRACT

A method of using a cleansing composition for cleansing a quantitatively aspirating sampling probe in an automated hematological analyzer is disclosed. The cleansing composition employed in the method is formulated to cleanse instantaneously on contact, and practically eliminates carry-over of hematological sample material, assaying reagents or of the cleansing composition itself. The cleansing composition is an acidic aqueous solution of pH 5.0 or less, including (1) a substance having a primary amino group; and (2) one or more nonionic surfactants selected from the group consisting of polyoxyethylene alkyl ether, polyoxyethylene alkyl phenyl ether, polyoxyethylene alkyl ester and polyoxyethylene sorbitan ester. Assay-material contaminated surfaces of the sampling probe are contacted with a cleansing amount of the cleansing composition.

4 Claims, 1 Drawing Sheet

HEMATOLOGICAL ANALYZER SAMPLING PROBE CLEANSING METHOD

This is a division of application Ser. No. 09/161,672, filed Sep. 29, 1998, now U.S. Pat. No. 6,043,205.

TECHNICAL FIELD

The present invention relates to a cleansing method for use in an automated hematological analyzer. The invention more particularly relates to a method for cleansing a quantitatively aspirating sampling probe in an automated hematological analyzer capable of simultaneous, multi-item analysis.

BACKGROUND ART

Clinical analytical procedures are increasingly becoming automated owing to technological advances, such that, for example, multiple items can be assayed by several different reagents simultaneously in one device. The extent of clinical monitoring items in the area of hemostasis and thrombosis does not end merely with blood coagulation time, but ramifies into quantitating the factors in the clotting/fibrinolytic system, and to quantitating fibrin degradation products; and it is now possible to make these measurements with a single device.

Automated hematological analyzers accordingly are able to investigate any hemostatic disorder, as well as risk of thrombosis. That is, by performing multiple assays on hematological samples, "coagulation profiles" are produced, from which bleeding disorders as well as the potential for pathological formation of cardiovascular blood clots (thrombi) can be evaluated.

Coagulation assays are performed in the hematological analyzer by mixing test reagents into hematological samples in reaction tubes and monitoring for diagnostic change; typically the time to onset of clotting in the sample is measured.

In human blood coagulation, in the pathway common to both the intrinsic (plasma-mediated) and extrinsic (tissue-mediated) pathways, the protease Factor X (Stuart Factor) is activated, which in turn activates prothrombin, by cleaving it to yield thrombin. Thrombin in turn cleaves fibrinogen to yield clot-forming fibrin.

Tissue factor (TF), released from tissues exposed to plasma from a ruptured blood vessel, can activate Factor X directly. Accordingly, a laboratory blood coagulation test known as the prothrombin time (PT) assay can be conducted to evaluate the extrinsic and common pathways. A test reagent containing tissue factor (also called thromboplastin) is added to a plasma sample, activating Factor X via the extrinsic route. The time to clot formation in the sample following the addition of the thromboplastin reagent is measured as the PT.

An evaluation of the integrity of the intrinsic pathway is by assaying for Factor VIII (antihemophilic factor), which for example can test for hemophilia. Factor VIII functions with other coagulation cascade proteases and calcium ions to activate Factor X. Accordingly, a Factor VIII reagent may be added to a plasma sample and, as with the PT test, the time to clotting monitored, except that therein the intrinsic pathway is evaluated.

On the other hand, clot-forming fibrin, the protein end product of blood coagulation, must eventually be degraded, which occurs through factors having fibrinolytic functions. Plasmin is the activated enzyme responsible for fibrin degradation in the fibrinolytic system, and is derived from converted plasminogen in the blood. Plasmin activity is in turn regulated by $\alpha_2$-antiplasmin, a principal inhibitor of fibrinolysis. Monitoring plasmin levels can accordingly indicate hemostatic integrity or thrombosis.

By the same token, antiplasmin levels can be assayed to evaluate fibrinolytic function. For example, by adding a plasmin-containing reagent to a hematological sample in a reaction tube, antiplasmin can then be quantitated.

Furthermore, the blood coagulation system must be regulated to prevent massive formation of thrombi. Blood consequently contains natural clotting cascade inhibitors.

Protein C is a coagulation inhibitor, functioning to lock the activity of activated Factor VIII, as well as another clotting factor. At the same time, Protein C inactivates an inhibitor of tissue plasminogen activator (tPA is secreted primarily by endothelial cells and activates plasmin), thus enhancing fibrinolytic activity.

Levels of Protein C can be assayed by adding to a sample a chromogenic synthetic peptide substrate that is cleaved in the presence of the reaction between a protease (Factor VIII, for example) and its inhibitor (Protein C, for example). Cleavage of the synthetic substrate produces a chromogenic change that can be quantitated photometrically.

The intrinsic clotting pathway by definition can be activated solely by elements within the blood itself, when intrinsic Factor XII (Hageman Factor) comes into contact with and is bound by a negatively charged surface (thus the pathway can be triggered in vitro). The time to coagulation via this mechanism is referred to as the "partial thromboplastin time," in relation to the time to coagulation required when the extrinsic pathway is initiated via thromboplastin.

The intrinsic clotting system can be screened generally for abnormalities by the activated partial thromboplastin time (aPTT) assay. This test is also used to monitor the anticoagulant effect of heparin treatment. Heparin occurs naturally in the basophils of blood leukocytes, but is prepared as a commercial product from animal sources and administered therapeutically. Heparin accelerates the activity of Antithrombin III (ATIII). ATIII is the major inhibitor of the enzymes of the clotting cascade, binding to some half-dozen proteases, including factors X and XII and thrombin. Antithrombin III acting with co-factor heparin functions immediately to inhibit coagulation.

The aPTT assay is conducted by adding a test reagent containing a Factor XII activator to a platelet-poor plasma sample. Time to clotting is evaluative of adequate levels of the intrinsic coagulation factors.

Antithrombin III levels can be assayed by employing a synthetic peptide substrate as with the assay for Protein C levels described above.

In the above-described automated hematological analyzers, measuring reagents and test samples are taken up by means of a pipette-like aspirating device (sampling probe) and ejected into reaction vessels.

Ideally, pipette devices used herein would be provided according to use, as it were, for each particular assaying reagent or each particular sample. However, due to cost and apparatus size limitations, a single pipette device is utilized in common. Herein, if the pipette device is not cleaned sufficiently the problem of "carry-over" occurs, in which prior-remaining matter is mixed in with next-aspirated reagents, exerting an influence on the analytical results.

In hemostasis and thrombosis assays, methods include clotting time and chromogenic substrate tests, as described above, as well as immunoassays. Among the reagents employed in these assaying methods are many that have enzymatic activity, or in the case of chromogenic substrates, that contain proteins or peptides. Because enzymes, and proteins and peptides generally, tend to become adsorbed on the pipette device, carry-over problems are liable to arise with the use of such reagents, making sufficient cleaning of the pipette device necessary. Conventionally the pipette device has been cleaned with a cleansing fluid containing a hypochlorite substance.

Nevertheless, there are situations in which using the above-noted cleansing fluid insufficiently cleans the pipette device in the automated analyzer. This has been particularly so with the foregoing plasmin-containing anti-plasmin assaying reagents, and PT reagents containing recombinant tissue factor. Moreover, increasing the concentration of the hypochlorite substance is not satisfactory, since this damages the tubes and other fluid components, or else brings about effects due to the residual hypochlorite substance itself. Further, the undesirability of a drop in processing capacity (throughput) of the automated analyzer due to the cleaning process therefore demands instantaneous cleansing.

SUMMARY OF THE INVENTION

An object of the present invention is to enable instantaneous cleaning of a sampling probe in an automated analyzer, and at the same time to curtail carry-over effects from the cleansing agent or from assaying reagents residual in the sampling probe due to insufficient cleaning.

Another object of the invention is to cleanse a pipette or sampling probe employed in aspirating and dispensing aliquots of analytical samples, assaying reagents, and reaction solutions thereof for multiple assays in an automated analyzer, by a method of contacting surfaces of the pipette or sampling probe at least subsequent to each assay with a specially prepared cleansing composition, so as to remove instantaneously assaying reagents such as enzymes, proteins and peptides contaminating the surfaces of the pipette or sampling probe, without contaminating the surfaces with the cleansing composition itself.

The specially prepared cleansing composition is an acidic aqueous solution of pH 5.0 or less; preferably the pH is about 1.8 to 4.0; most preferably the pH is about 2.0 to 2.5. In order to maintain acidic pH, adjustment can be made utilizing conventional acidifying agents (hydrochloric acid, phosphoric acid, citric acid, for example), and buffers (Goode buffers, for example). The amount of acid added to he composition depends on the desired pH, and the concentration and strength of the acid.

As a substance having a primary amino group, amino acids, and "Tris" [tris(hydroxymethyl)aminomethane] or the like can be used. The amino acids are not particularly limited, however glycine, valine, leucine, phenylalanine, alanine, serine, and threonine are preferable; glycine is most preferable. The concentration of the compound having a primary amino group can be suitably determined according to the compound employed; but for example, amino acids can be employed in a concentration in the range of 0.05 to 10 w/v %, more preferably in the range of 0.1 to 2.0 w/v %.

Furthermore, a small amount of nonionic surfactant elevates the cleansing effectiveness of the composition. For example, polyoxyethylene alkyl ethers, polyoxyethylene alkyl phenyl ethers, polyoxyethylene sorbitan esters, polyoxyethylene alkyl esters, and mixtures thereof can be used. If the nonionic surfactant is water soluble, the ethylene oxide or polyoxyethylene molar addition number is not particularly limited; however 2 to 100 moles is preferable, 5 to 60 moles is more preferable, and 5 to 12 moles is most preferable. The cleansing effectiveness is elevated further by mixing a nonionic surfactant of low ethylene oxide molar addition number with one of high ethylene oxide molar addition number.

The polyoxyethylene alkyl ether, polyoxyethylene alkyl phenyl ether and polyoxyethylene alkyl ester include an alkyl group having 8 to 20 carbons, and preferably an alkyl group having 8 to 18 carbons.

Several commercially produced nonionic surfactants suitable for use in the specially prepared composition are available. For example, polyoxyethylene alkyl ether in several ethylene oxide molar addition numbers is available as Actinol L™ (Matsumoto Yushi Pharmaceuticals, Inc.), and Noigen ET™ (Daiichi Kogyo Pharmaceuticals, Inc.); polyoxyethylene alkyl phenyl ether in several ethylene oxide molar addition numbers is available as Emulsit™ (Daiichi Kogyo Pharmaceuticals, Inc.), and Nonipol™ (Sanyo Kasei Kogyo, Inc.); polyoxyethylene sorbitan ester in several ethylene oxide molar addition numbers is available as Span™ (Atlas Powder Co.), and Solubon™ (Toho Kagaku Kogyo, Inc); polyoxyethylene alkyl ester in several ethylene oxide molar addition numbers is available as Noigen ES™ (Daiichi Kogyo Pharmaceuticals, Inc). Furthermore, the concentration of the nonionic surfactant can be suitably determined according to the employed surfactant; but the surfactant can be employed in the range of 0.001 to 2.0 w/v %, and more preferably in the range of 0.10 to 1.00 w/v %.

The cleansing method of the present invention is extremely effective in instantaneously cleansing the quantitatively aspirating pipette or sampling probe wherein concurrent multi-item analysis is conducted by an automated analyzer having a liquid dispensing system.

After the sampling probe dispenses a reagent in the process of assaying one test item, the aspirating probe which has aspirated/ejected sample aliquots and reagents, or their reaction solution, is cleansed with the specially prepared cleansing composition, and a rinse is performed as desired. The pipette being cleansed draws in an amount of the cleansing composition sufficient to contact substantially all contaminated surfaces thereof and then discharges the spent cleansing composition to a suitable waste site. Optionally the pipette can be rinsed with a conventional rinse solution, such as water. Subsequently analysis is carried out on another assay item. It is sufficient to have an extremely short period for the exposure of the aspirating probe to the cleansing composition. The preferable duration of the exposure is about 0.1 to 20 seconds, and more preferably about 0.2 to 1.0 seconds. The specially prepared cleansing composition may be used in combination with other types of cleansing compositions, for example, with hypochlorite cleansing compositions.

As an example of a preferred chemical form for the specially prepared cleansing composition, hydrochloric acid glycine (polyoxyethylene)$_n$ nonyl phenyl ether can be given. Glycine can be replaced with valine, leucine, phenylalanine, alanine, serine, or threonine. Furthermore, hydrochloric acid can be replaced with acetic acid or citric acid.

The cleansing composition in the method according to the present invention is superior in preventing carry-over of reagents remaining in the pipette or sampling probe wherein multiple assays including those having enzymatic activity, or employing proteins or the peptides of chromogenic substrates, are carried out continuously, such as is the case with automated devices for carrying out hemostasis or thrombosis analysis.

The foregoing and other objects, features, aspects and advantages of the present invention will become more apparent from the following detailed description, illustrated by way of the following examples.

DETAILED DESCRIPTION OF THE INVENTION

Figure 1:
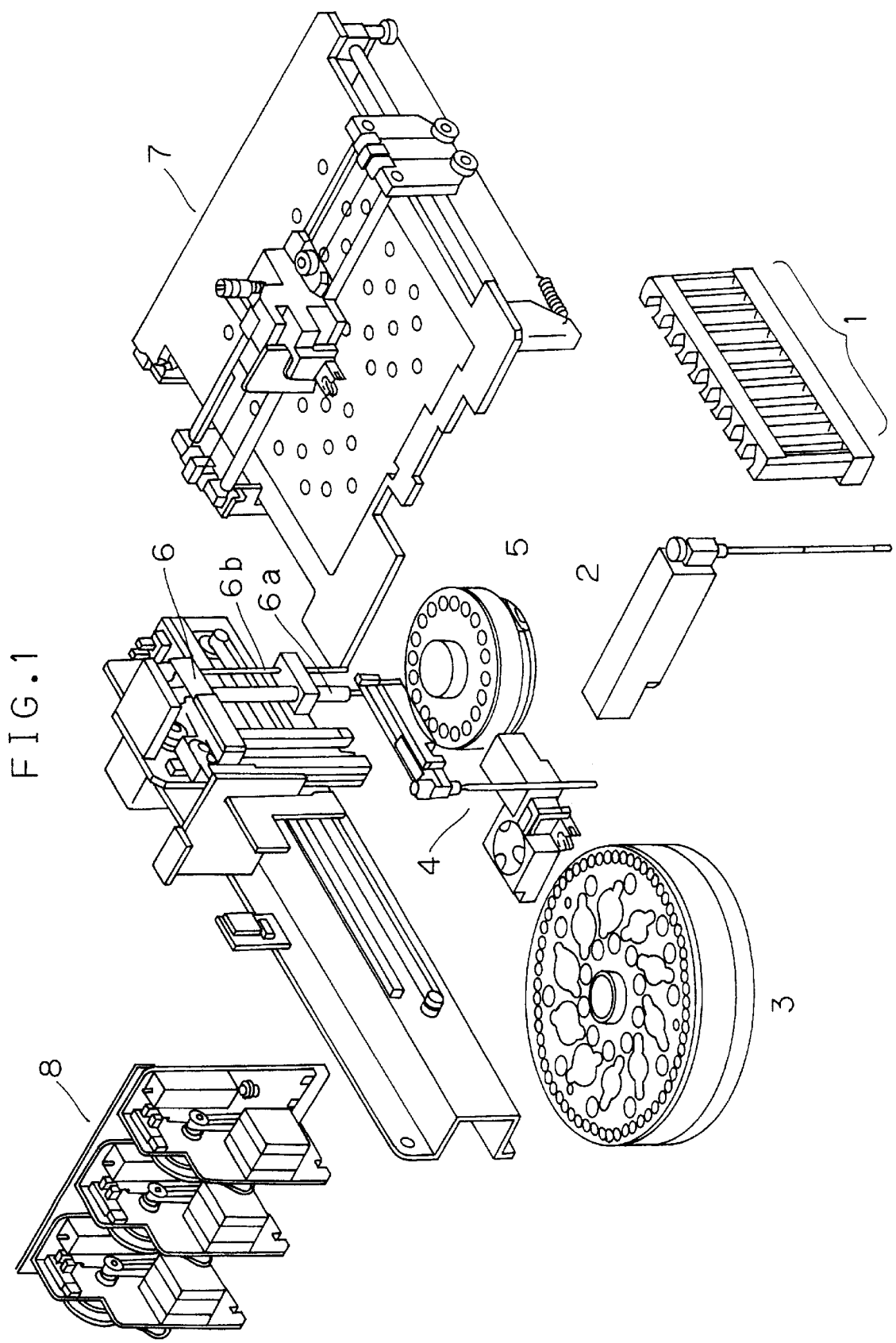
FIG. 1 is an exploded, oblique view schematically illustrating an automated hematological analyzer, in which a method in accordance with the present invention may be utilized.

Analysis flow in an automated hematological analyzer will be described with reference to FIG. 1. Centrifuged blood sample tubes are arranged in a sample rack 1. When the analytical procedure begins, requisite sample aliquots are aspirated from the sample tubes by sampling arm 2 and dispensed into a main reagent refrigeration unit 3, wherein the samples and reagents are kept refrigerated to suppress degradation. Next, for each assay item, sampling arm 4 aspirates and dispenses a sample aliquot, which is then incubated in a sample-heating unit 5. After a fixed time, an assaying reagent is dispensed with reagent-aspirating pipette (quantitative sampling probe) arm 6 (in the figure, the thick pipette 6a has a heater, and the slender pipette 6b is exclusively for thrombin) into the incubated sample aliquot. Herein, XY mechanism 7 functions as a stirrer to mix the reagents and samples sufficiently. XY mechanism 7 then transports the samples to a (not-shown) photometric unit. The assayed samples are then disposed of, again by XY mechanism 7, after which the analytical procedure is complete.

EXAMPLE 1

| Cleansing Preparation Composition I | |
|---|---|
| glycine | 0.25 w/v % |
| 6N hydrochloric acid | 0.31 v/v % |
| Emulsit 16 [(polyoxyethylene)$_n$ nonyl phenyl ether, n = 40] | variable conc. |
| pH | 2.2 |

Demonstrated Cleansing Effectiveness Test Data

Cleansing Effectiveness Depending on Difference in Concentration of "Emulsit 16"

Procedure

In an Automated Blood Coagulation Analyzer CA-6000, manufactured by Toa Medical Electronics Co., Ltd., highly abnormal prothrombin time (PT) plasma sample aliquots were initially assayed with Dade Co.'s "Innovin," a PT assaying reagent containing recombinant tissue factor. Then, utilizing a Factor VIII quantitating reagent, Factor VIII quantitation of further sample aliquots was conducted. In these analyses, clotting time was obtained by photometrically detecting, as a change in intensity of diffused light, the change in turbidity due to the fibrin clot that arises when sample and reagent are mixed. Following the analysis with "Innovin," the degree of the carry-over from the PT reagent to the Factor VIII quantitating reagent was examined (a) wherein the reagent-aspirating pipette was not cleaned, (b) wherein the reagent-aspirating pipette was cleaned utilizing a conventional cleansing composition having a hypochlorite concentration of about 1.0 w/v %, and (c) wherein the reagent-aspirating pipette was cleansed utilizing cleaning solutions which were prepared by varying the concentration of "Emulsit 16" in the above Composition I.

For each of these respective cases, the resultant clotting times in the Factor VIII assay, as well as activeness percentages are indicated below. The activeness percentages of the samples were calculated from a previously obtained calibration curve relating clotting time and activeness percentage. The result of Factor VIII quantitation independently without assaying with "Innovin" was used as the control value.

Results

| | Cleansing Method | Factor VIII Quantitation | |
|---|---|---|---|
| | | Clotting Time | Activeness Percentage |
| | Control | 125.4 s | 0.4% |
| a) | Reagent pipette not cleansed | 50.2 s | 559.2% |
| b) | Cleansed with hypochlorite cleansing agent | 72.0 s | 54.2% |
| c) | Cleansed with Composition I using Emulsit 16, changing concentrations | | |
| | Emulsit 16 0.01 w/v % | 78.8 s | 30.2% |
| | Emulsit 16 0.10 w/v % | 105.9 s | 2.7% |
| | Emulsit 16 0.25 w/v % | 109.9 s | 1.9% |
| | Emulsit 16 0.50 w/v % | 110.0 s | 1.9% |

With the clotting time control measurement in the Factor VIII assay 125.4 sec., a tendency to extreme prolongation was indicated, against which a tendency to shortening was indicated, due to carry-over of the PT reagent, (a) wherein the pipette was not cleaned, and (b) wherein it was cleaned utilizing the conventional hypochlorite cleansing composition, with clotting times in the Factor VIII assay 50.2 sec. and 72.0 sec., respectively.

On the other hand, (c) wherein the pipette was cleansed with cleansing solutions prepared from Composition I, changing concentrations of "Emulsit 16," with a 0.10 w/v % concentration or more, a tendency to prolongation in clotting times in the Factor VIII assay was indicated. Comparing the activeness percentages with the value of the control measurement also yields similar results. In short, carry-over of the PT reagent could be prevented.

EXAMPLE 2

| Cleansing Preparation Composition II | |
|---|---|
| glycine | 0.25 w/v % |
| 6N hydrochloric acid | 0.31 v/v % |
| Emulsit [(polyoxyethylene)$_n$ nonyl phenyl ether, variable molar addition number] | 0.25 w/v % |
| pH | 2.2 |

Demonstrated Cleansing Effectiveness Test Data

Cleansing Effectiveness Depending on Difference in Polyoxyethylene Molar Addition Number in "Emulsit"

Procedure

In the Automated Blood Coagulation Analyzer CA-6000, highly abnormal prothrombin time (PT) plasma sample aliquots were initially assayed with "Innovin." Then, utilizing a Factor VIII quantitating reagent, Factor VIII quantitation of further sample aliquots was conducted. In these analyses, clotting time was obtained by photometrically detecting as a change in intensity of diffused light the change in turbidity due to the fibrin clot that arises when sample and reagent are mixed. Following the analysis with "Innovin," the degree of the carry-over from the PT reagent to the Factor VIII quantitating reagent was examined (a) wherein the reagent-aspirating pipette was not cleaned, (b) wherein the reagent-aspirating pipette was cleaned utilizing a conventional cleansing composition having a hypochlorite concentration of about 1.0 w/v % and (c) wherein the reagent-aspirating pipette was cleansed utilizing cleaning solutions which were prepared by varying polyoxyethylene molar addition numbers in "Emulsit" in the above Composition II.

For each of these respective cases, the resultant clotting times in the Factor VIII assay, as well as activeness percentages are indicated below. The result of Factor VIII quantitation independently without assaying with "Innovin" was used as the control value.

Results

| | Cleansing Method | Factor VIII Quantitation | |
|---|---|---|---|
| | | Clotting Time | Activeness Percentage |
| | Control | 125.4 s | 0.4% |
| a) | Reagent pipette not cleansed | 50.2 s | 559.2% |
| b) | Cleansed with hypo-chlorite cleansing agent | 72.0 s | 54.2% |
| c) | Cleansed with Composition II using Emulsit, changing polyoxyethylene molar addition number | | |
| | Emulsit 9 (n = 30) 0.25 w/v % | 112.3 s | 1.5% |
| | Emulsit 16 (n = 40) 0.25 w/v % | 110.2 s | 1.8% |
| | Emulsit 25 (n = 50) 0.25 w/v % | 100.6 s | 4.3% |
| | Emulsit 100 (n = 100) 0.25 w/v % | 85.2 s | 17.0% |

With the clotting time control measurement in the Factor VIII assay 125.4 sec., a tendency to extreme prolongation was indicated, against which a tendency to shortening was indicated, due to carry-over of the PT reagent, (a) wherein the pipette was not cleaned, and (b) wherein it was cleaned utilizing the conventional hypochlorite cleansing composition, with clotting times in the Factor VIII assay 50.2 sec. and 72.0 sec., respectively.

On the other hand, (c) wherein the pipette was cleansed with cleansing solutions prepared from Composition II, changing polyoxyethylene molar addition numbers in "Emulsit," with the addition number n=50 or less, a tendency to prolongation in clotting times in the Factor VIII assay was indicated. Comparing the activeness percentages with the value of the control measurement also yields similar results. In short, carry-over of the PT reagent could be prevented.

EXAMPLE 3

Cleansing Preparation Composition III

| glycine | 0.25 w/v % |
|---|---|
| 6N hydrochloric acid | 0.31 v/v % |
| Emulsit 16 [(polyoxyethylene)$_n$ nonyl phenyl ether, n = 40] | 0.25 w/v % |
| Nonipol [(polyoxyethylene)$_n$ nonyl phenyl ether, variable molar addition number] | 0.25 w/v % |
| pH | 2.2 |

Demonstrated Cleansing Effectiveness Test Data

Cleansing Effectiveness Depending on Supplementation of Non-Ionic Surfactant of Low Polyoxyethylene Molar Addition Number Procedure In the Automated Blood Coagulation Analyzer CA-6000, highly abnormal prothrombin time (PT) plasma sample aliquots were initially assayed with "Innovin." Then, utilizing a Factor VIII quantitating reagent, Factor VIII quantitation of further sample aliquots was conducted. In these analyses, clotting time was obtained by photometrically detecting as a change in intensity of diffused light the change in turbidity due to the fibrin clot that arises when sample and reagent are mixed. Following the analysis with "Innovin," the degree of carry-over from the PT reagent to the Factor VIII quantitating reagent was examined (a) wherein the reagent-aspirating pipette was not cleaned, (b) wherein the reagent-aspirating pipette was cleaned utilizing a conventional cleansing composition having a hypochlorite concentration of about 1.0 w/v % and (c) wherein the reagent-aspirating pipette was cleaned utilizing cleaning solutions prepared supplementing non-ionic surfactants of low polyoxyethylene molar addition number in cleansing compositions from the above Composition III.

For each of these respective cases, the resultant clotting times in the Factor VIII assay, as well as activeness percentages are indicated below. The result of Factor VIII quantitation independently without assaying with "Innovin" was used as the control value.

Results

| | Cleansing Method | Factor VIII Quantitation | |
|---|---|---|---|
| | | Clotting Time | Activeness Percentage |
| | Control | 128.1 s | 0.3% |
| a) | Reagent pipette not cleansed | 51.2 s | 492.2% |
| b) | Cleansed with hypo-chlorite cleansing agent | 73.5 s | 47.4% |
| c) | Cleansed with Composition III including supplemental non-ionic surfactants of low polyoxy-ethylene molar addition number | | |
| | Nonipol 55 (n = 5.5) 0.25 w/v % | 126.1 s | 0.4% |
| | Nonipol 70 (n = 7) 0.25 w/v % | 128.3 | 0.3% |
| | Nonipol 90 (n = 9) 0.25 w/v % | 125.7 s | 0.4% |
| | Nonipol 100 (n = 10) 0.25 w/v % | 126.6 s | 0.4% |
| | Nonipol 120 (n = 12) 0.25 w/v % | 128.1 s | 0.3% |

With the clotting time control measurement in the Factor VIII assay 128.1 sec., a tendency to extreme prolongation was indicated, against which a tendency to shortening was indicated, due to carry-over of the PT reagent, (a) wherein the pipette was not cleaned, and (b) wherein it was cleaned utilizing the conventional hypochlorite cleansing composition, with clotting times in the Factor VIII assay 51.2 sec. and 73.5 sec., respectively.

On the other hand, (c) wherein the pipette was cleansed with cleansing solutions prepared from Composition III, supplementing non-ionic surfactants of low polyoxyethylene molar addition number, n=5.5 to 12, a tendency to prolongation in clotting times in the Factor VIII assay was indicated. Comparing the activeness percentages with the value of the control measurement also yields similar results. In short, carry-over of the PT reagent could be prevented.

EXAMPLE 4

| Cleansing Preparation Composition IV | |
|---|---|
| glycine | 0.25 w/v % |
| 6N hydrochloric acid | 0.31 v/v % |
| Emulsit 16 [(polyoxyethylene)$_n$ nonyl phenyl ether, n = 40] | 0.25 w/v % |
| Nonipol [(polyoxyethylene)$_n$ nonyl phenyl ether, n = 7] | 0.25 w/v % |
| pH | variable |

Demonstrated Cleansing Effectiveness Test Data

Cleansing Effectiveness Depending on Cleaning Solution pH

Procedure

In the Automated Blood Coagulation Analyzer CA-6000, anti-plasmin in sample aliquots of normal human plasma was initially assayed utilizing an anti-plasmin assaying reagent containing plasmin. Then, a Protein C activity analysis of sample aliquots was conducted employing a chromogenic substrate procedure. Following assay by the anti-plasmin reagent, the degree of the carry-over of the anti-plasmin reagent to Protein C activity analysis was examined (a) wherein the reagent-aspirating pipette was not cleaned, (b) wherein the reagent-aspirating pipette was cleaned utilizing a cleansing composition having a hypochlorite concentration of about 1.0 w/v % and (c) wherein the reagent-aspirating pipette was cleaned utilizing cleaning solutions prepared varying the pH in cleansing compositions from the above Composition IV by adding 1N NaOH accordingly.

For each of these respective cases, the Protein C activeness percentages are indicated below. The result for Protein C activeness independently without assaying with antiplasmin was used as the control value.

| | Results | |
|---|---|---|
| | Cleansing Method | Protein C Activeness |
| | Control | 102.5% |
| a) | Reagent pipette not cleansed | 160.0% |
| b) | Cleansed with hypo-chlorite cleansing agent | 152.0% |
| c) | Cleansed with Composition IV, changing pH of cleaning solution | |
| | pH 2.0 | 103.5% |
| | pH 4.0 | 101.2% |
| | pH 5.0 | 108.0% |
| | pH 9.0 | 125.8% |
| | pH 12.0 | 138.9% |

In the control measurement, Protein C activeness displayed a normal value of 102.5%, against which (a) wherein the pipette was not cleaned, and (b) wherein it was cleaned utilizing the conventional hypochlorite cleansing composition, a tendency to abnormally high Protein C activeness values, 160.0% and 152.0%, respectively, was exhibited, due to carrying-over of antiplasmin reagent.

On the other hand, (c) wherein the pipette was cleansed with cleansing solutions prepared from Composition IV, changing the pH, from pH 5.0 to 2.0, Protein C activeness normalized, yielding results similar to the value of the control measurement. In short, carry-over of the anti-plasmin reagent could be prevented.

EXAMPLE 5

| Cleansing Preparation Composition V | |
|---|---|
| glycine | 0.25 w/v % |
| 6N hydrochloric acid | 0.31 v/v % |
| Emulsit 16 [(polyoxyethylene)$_n$ nonyl phenyl ether, n = 40] | 0.25 w/v % |
| Nonipol [(polyoxyethylene)$_n$ nonyl phenyl ether, n = 7] | 0.25 w/v % |
| pH | 2.2 |

Demonstrated Cleansing Effectiveness Test Data

Effectiveness of Cleansing Solution in Preventing Carry-Over in Various Assays

Procedure

In the Automated Blood Coagulation Analyzer CA-6000, utilizing reagents (A) in inducing carry-over and reagents (B) to incur carry-over, concurrent two-item assays were conducted. Following assay utilizing the reagent for inducing carry-over, (a) wherein the reagent-aspirating pipette was not cleaned, and (b) wherein the pipette was cleaned utilizing a cleansing composition from the above Composition V, the degree of carry-over from reagent (A) to reagent (B) was examined. The result assayed independently with reagent (B) was taken as the control value.

| | | | | Results | |
|---|---|---|---|---|---|
| Reagent A | Reagent B | Sample | Control | Without Cleansing | With Cleansing |
| Recombinant PT | aPTT | Heparin-Added Plasma | 118.3 s | 70.3 s | 118.0 s |
| Recombinant PT | Factor VIII | Normal Human Plasma | 100.0% | 595.0% | 99.8% |
| Anti-plasmin | aPTT | Normal Human Plasma | 31.7 s | 36.6 s | 31.8 s |
| Anti-plasmin | Protein C | Normal Human Plasma | 102.0% | 163.0% | 102.5% |
| ATIII | aPTT | Normal Human Plasma | 31.6 s | 38.3 s | 31.5 s |
| ATIII | Protein C | Normal Human Plasma | 102.0% | 50.0% | 103.5% |

Comparing against the control value the results from the measurements carried out without cleansing the reagent-aspirating pipette between assays demonstrates striking differences. In contrast, cleansing the pipette between assays yielded results similar to the value of the control measurement. In short, carry-over of reagent A to reagent B could be prevented by a cleansing composition from Composition V.

A cleansing method in accordance with the present invention practically eliminates carry-over, securing accuracy of analytical results, particularly in hemostatic and thrombotic assays employing enzymatically active or peptidyl reagents.

Various details of the present invention may be changed without departing from its spirit nor its scope. Furthermore, the foregoing description of the embodiments according to the present invention are provided for illustration only, and not for the purpose of limiting the invention as defined by the appended claims and their equivalents.

What is claimed is:

1. A method for cleansing a pipette in an automated analyzer for analyzing multiple assay items simultaneously, having quantitatively aspirating pipettes for aspirating and dispensing assay material aliquots including analytical samples, assaying reagents, and reaction solutions thereof, said method comprising:

dispensing assay material from a quantitatively aspirating pipette;

subsequently contacting assay-material contaminated surfaces of the pipette with a cleansing amount of a cleansing composition for cleansing the pipette, wherein the cleansing composition is an acidic aqueous solution of pH 5.0 or less and includes (1) a compound having a primary amino group; and
(2) one or more nonionic surfactants selected from the group consisting of polyoxyethylene alkyl ethers, polyoxyethylene alkyl phenyl ethers, polyoxyethylene alkyl esters and polyoxyethylene sorbitan esters.

2. A method as set forth in claim 1, wherein the quantitatively aspirating pipette is in contact with said cleansing composition for approximately 0.1 to 20 seconds.

3. A method as set forth in claim 1, wherein the quantitatively aspirating pipette is in contact with said cleansing composition for approximately 0.2 to 1.0 seconds.

4. A method as set forth in claim 1, wherein the quantitatively aspirating pipette is for analysis in hemostasis and thrombosis assays.

* * * * *